(12) United States Patent
Gombart et al.

(10) Patent No.: US 8,013,204 B2
(45) Date of Patent: Sep. 6, 2011

(54) USE OF PARTLY PREHYDRATED LIME FOR SEPARATING A SOLID MATTER/LIQUID MIXTURE, METHOD FOR TREATING SLUDGE AND PURIFIED SLUDGE OBTAINED BY SAID METHOD

(75) Inventors: Marc Gombart, Ardon (FR); Jean-Yves Tilquin, Villers-le-Bouillet (BE); Stéphane Bartiaux, Tournai (BE)

(73) Assignees: Sicab-Carmeuse France (FR); Marc Gombart (FR)

( * ) Notice: Subject to any disclaimer, the term of this patent is extended or adjusted under 35 U.S.C. 154(b) by 974 days.

(21) Appl. No.: 11/575,295

(22) PCT Filed: Sep. 6, 2005

(86) PCT No.: PCT/FR2005/002215
§ 371 (c)(1),
(2), (4) Date: May 25, 2007

(87) PCT Pub. No.: WO2006/030102
PCT Pub. Date: Mar. 23, 2006

(65) Prior Publication Data
US 2008/0028811 A1    Feb. 7, 2008

(30) Foreign Application Priority Data
Sep. 15, 2004    (FR) .................................... 04 09767

(51) Int. Cl.
*A62D 3/30*  (2007.01)
*A62D 3/32*  (2007.01)
*A62D 3/33*  (2007.01)
*A62D 3/36*  (2007.01)
*B03D 3/00*  (2006.01)
*B01D 21/01*  (2006.01)
*C02F 1/52*  (2006.01)
*C01F 5/02*  (2006.01)
*C01F 5/14*  (2006.01)
*C01F 11/02*  (2006.01)
*C01B 13/14*  (2006.01)

(52) U.S. Cl. ........ 588/313; 588/314; 588/315; 588/318; 210/723; 423/635; 423/640

(58) Field of Classification Search .......... 588/313–320, 588/400, 405–415
See application file for complete search history.

(56) References Cited

U.S. PATENT DOCUMENTS
5,573,348 A * 11/1996 Morgan .......................... 405/52
(Continued)

FOREIGN PATENT DOCUMENTS
EP    1 154 958 B1    11/2001
(Continued)

OTHER PUBLICATIONS

Uglea et al. "Sysnthesis and characterization of oligomers" CRC Press (1991) pp. 13-14.*
(Continued)

*Primary Examiner* — Jerry Lorengo
*Assistant Examiner* — Jennifer A Smith
(74) *Attorney, Agent, or Firm* — Ostrolenk Faber LLP

(57) ABSTRACT

A novel use of delayed reactivity partly prehydrated lime ("DRQL"), which is comprised of 40 to 98% by weight of CaO and of 60 to 2% by weight of Ca(OH)$_2$, preferably of 80 to 92% by weight of CaO and of 20 to 8% by weight of Ca(OH)$_2$, and more preferably of 85 to 90% by weight of CaO and of 15 to 10% by weight of Ca(OH)$_2$, in the field of the separation of solid matter from the liquid of a suspension. The invention also involves a novel method for treating a sludge, in which the solid matter is concentrated, dried and recovered using the delayed reactivity partly prehydrated lime. It additionally relates to, as a novel industrial product, the purified sludge obtained according to the method.

8 Claims, 1 Drawing Sheet

U.S. PATENT DOCUMENTS

2002/0152933 A1* 10/2002 Alain et al. .................... 106/724
2008/0028811 A1* 2/2008 Gombart et al. .................. 71/15

FOREIGN PATENT DOCUMENTS

| | | |
|---|---|---|
| FR | 2 841 895 | 1/2004 |
| FR | 2841895 A1 * | 1/2004 |
| JP | 60-54799 | 3/1985 |
| JP | 04144988 A * | 5/1992 |
| WO | WO 98/02391 | 1/1998 |
| WO | WO 00/47527 | 8/2000 |

OTHER PUBLICATIONS

International Search Report PCT/FR2005/002215 dated Mar. 9, 2006.

Letter dated May 26, 2009 from NV Gevers Patents S.A. on behalf of Lhoist Recherche et Developpement to the European Patent Office with Third-Party observations concerning Patent Publication No. 1 791 792 (Appln. No. 05 805 575.7-2104) corresponding to the present U.S. case.

European Patent Office Action (dated Sep. 28, 2010) issued with regard to Appln. No. 05 805 575.7-2104 corresponding to the present U.S. case.

Judgement of French Tribunal De Grande Instance De Paris in action by Lhoist against corresponding French Patent No. 2 875 228 (Appln. No. FR20040009767).

* cited by examiner

USE OF PARTLY PREHYDRATED LIME FOR SEPARATING A SOLID MATTER/LIQUID MIXTURE, METHOD FOR TREATING SLUDGE AND PURIFIED SLUDGE OBTAINED BY SAID METHOD

CROSS REFERENCE TO RELATED APPLICATION

The present application is a 35 U.S.C. §§371 national phase conversion of PCT/FR2005/002215, filed Sep. 6, 2005, which claims priority of French Patent Application No. 0409767 filed Sep. 15, 2004, which is herein incorporated by reference. The PCT Application was published in the French Language.

BACKGROUND OF THE INVENTION

1. Technical Field

The present invention relates to a novel use of partly prehydrated lime, which contains CaO that reacts with $H_2O$ after a certain lag phase, that is to say a delayed reactivity quicklime (abbreviated to: "DRQL"), in the field of separating solid matter from a mixture comprising said solids and a liquid (i.e. liquid/solid separation, denoted hereinafter for convenience by "solid matter/liquid separation" or "solids/liquid separation"), and in particular in the field of separating the solid matter from a suspension in a liquid. It also relates to a method for treating a sludge, in which the solids are concentrated, decontaminated, dried and recovered using said delayed reactivity partly prehydrated lime. Finally it relates, as novel industrial products, to (a) the purified sludge (denoted hereinafter by "solid material derived from a sludge") obtained according to this method, on the one hand, and to (b) the combination of a DRQL with at least one $Fe^{3+}$ and/or $Al^{3+}$ salt, which is used to carry out this method, on the other hand.

2. Discussion of the Prior Art

It is known that various techniques for solids/liquid separation have been developed in order to concentrate the solid matter contained in a solids/liquid mixture when at least one portion of said solids is dispersed in the liquid of said mixture, especially when they are in the form of suspensions of particles, such as is the case for sludges.

Said concentrated mixtures thus obtained, especially concentrated suspensions, must often undergo subsequent treatments before being able to be handled, stored or reused. These treatments use reactants whose role is, for example, to modify the chemical properties, to decontaminate (i.e. to sanitize or clean up) or else to modify the physical properties of the concentrated solid matter/liquid mixture or of the concentrated suspension, such as the rheology or the plasticity.

It is known that the final solids concentration of a solids/liquid mixture or of a suspension is an important factor that should be optimized in order to promote the implementation of the treatment, handling and storage steps. From this viewpoint, it has been proposed to improve the performances of the solid matter/liquid separation methods, for example:

- on the one hand, by means of a chemical treatment of the solid matter/liquid mixtures or of the suspensions resulting in precipitation and flocculation phenomena; and
- on the other hand, by optimizing the equipment itself, the term "equipment" here denoting the solids/liquid separation conditions and devices [in particular the centrifuges and filtration equipment such as filter presses (especially plate or tube filter presses) and belt filters (especially pressurized or vacuum belt filters)].

It is also known that lime may be used to improve the performance of the solid matter/liquid separation methods. It is in that case added to the suspension before the solid matter/liquid separation (in this case a person skilled in the art refers to this as "pre-liming", i.e. a liming operation before filtration, centrifugation or settling) or after said separation (in that case a person skilled in the art refers to this as "post-liming", i.e. a liming operation after filtration, centrifugation or settling).

Pre-Liming

Within the context of pre-liming, it is found that quicklime is not suitable when the solids/liquid mixture or suspension contains a liquid that reacts with it, such as water. This is because the violent reaction between quicklime and water (i) results in unhomogeneous mixtures, and (ii) disturbs the solid matter/liquid separation. Therefore it is preferred to introduce hydrated lime $Ca(OH)_2$ either in powder form or in the form of an aqueous suspension, into said mixture or said suspension to be concentrated. The $Ca(OH)_2$ particles, thus added or formed by reaction of the lime with the water from the solid matter/liquid mixture or from the suspension, have a size typically of less than 10 µm; these particles are too small to be able to increase the porosity of the separation residue or cake and thus to promote the desiccation and decontamination of the solid matter/liquid separation cake.

Even if the use of quicklime added in the form of larger particles is able to promote the centrifugation of the sludges by increasing the porosity of the filtration or centrifugation cake (as described in the article published in *Wat. Sci. Tech.*, 1993, Vol. 28 (No. 1), pp 223-231], the problem of the violent reaction between the lime and the water from the solid matter/liquid mixture or from the suspension, which is not resolved, remains unacceptable.

It is known from the article by S. DENNEUX-MUSTIN et al., *Wat. Res.*, 2001, vol. 35 (No. 12), pp 3018-3024, that the use of lime combined with $FeCl_3$ promotes the mechanical dehydration of the sludges. This effect is also observed when the lime is added alone to a sludge that already contains iron as described in WO 99/10288 A.

It is also known that, during the use of organic polymer flocculants, the addition of lime generates a high pH that causes, in most cases, their inactivation or destruction by alkaline hydrolysis. The granted patent EP 1 154 958 B proposes to get round this difficulty by controlling or delaying the increase of the pH; to that effect, the recommended solution comprises the addition, to the sludge to be concentrated, of an organic flocculant and a particular lime within the context of pre-liming, said lime being chosen from the group formed (according to the wording of claim 1 of said patent) by:

quicklime;
hydrated lime in powder form;
hydrated lime in suspension in water, having a particle size $d_{50} \geq 50$ µm;
overburnt lime;
quicklime containing a fluid additive having an ability to agglomerate fine particles;
quicklime containing a hydration-retarding agent;
hydrated lime having elementary agglomerated particles;
hydrated lime to which an agent has been added for slowing down the activity [i.e., according to the language used by EP 1 154 958 B in paragraph [0019], a product that slows down the dissolution of $Ca(OH)_2$ in water];
hydrated lime having a solids content greater than 20% by weight; and "unfilled" lime [i.e. a lime from which the fine particles have been removed, in particular those having a size of less than or equal to 200 μm].

The description of EP 1 154 958 B points out, in addition, the possibility of requiring a DRQL for the pre-liming operation (see, to that effect, the last sentence of paragraph [0026] of this patent) in order to slow down the slaking reaction. However this patent neither describes nor suggests the feature of the present invention, mainly that said DRQL intervenes in the agglomeration of solids during the pre-liming operation; then in the post-liming operation for the desiccation and decontamination of the solids contained in the sludges.

Post-Liming

Furthermore, the use of quicklime, during the post-liming of the concentrated solid matter/liquid mixtures or concentrated suspensions each containing water, certainly has numerous advantages. It is known, in particular, from WO 02/32818 A that the increase of the pH and of the temperature associated with the reaction of the quicklime with the residual water contained in the wet separation cakes ensures their sanitization. This is because, besides the fact of generating heat, it is found that the reaction (1) between water and quicklime:

$$CaO + H_2O \rightarrow Ca(OH)_2 \quad (1)$$

consumes the water and makes it possible to increase the level of dryness of the separation cake, as indicated in U.S. Pat. No. 4,279,279 A, the quicklime CaO actually being capable of capturing around 32% of its weight in water.

However, as in the case of the pre-liming, it is also difficult to obtain in post-liming a homogeneous mixture due to the violence of the aforementioned reaction (1). In addition, the post-liming requires an additional step, namely the mixing of said concentrated solid matter/liquid mixture, or of said concentrated suspension, with the quicklime. This mixing step has the drawback of increasing the cost and the complexity of the operating conditions, on the one hand, and of disintegrating said concentrated solid matter/liquid mixture or said concentrated suspension, forming the separation cake, by the mechanical stresses that it generates, on the other hand.

The drawback linked to the increase in the number of steps for treating the separation cake is found in U.S. Pat. No. 5,679,262 A, which describes a post-liming technique consisting of two steps. This technique certainly enables the quantity of quicklime required for treating a sludge to be reduced by 40%, but has the disadvantage of making the processing conditions of said treatment more complex.

DRQL

Furthermore, delayed reactivity partly prehydrated quicklimes (DRQLs) are known. These products are formed from CaO and from $Ca(OH)_2$. They are in the form of a mixture of quicklime CaO particles and hydrated lime $Ca(OH)_2$ particles, arranged in such a way that, in the presence of water, the aforementioned reaction (1) is delayed. In the current state of knowledge, there is every reason to presume that the DRQL is in the form of quicklime CaO particles, forming a core, and of hydrated lime $Ca(OH)_2$ particles, forming a temporarily protective layer or film covering the CaO core. Even though this is a theory that does not tie the Applicant, the description "CaO core covered with a temporarily protective $Ca(OH)_2$ membrane or layer" is particularly practical for understanding the delay mechanism of the reaction (1). On this subject, the granted French application FR 2 841 895 A proposes, in particular, a DRQL that can be used, as a binding agent for compacting a mineral filler (such as clay, earth, cement, sludges and mixtures thereof) in the manufacture of shaped articles. According to the teaching of FR 2 841 895 A, said DRQL is involved, in the manufacture of said shaped articles, in the form of a powder or, thanks to the addition of a plasticizer (denoted "superplasticizer" by a person skilled in the art), in the form of a fluid aqueous suspension and, where appropriate, it is concentrated.

Compacting

Compacting (especially according to JP 60/054799 A or the aforementioned FR 2 841 895 A) of a waste, such as a sludge, should not be confused with the pre-liming operation or the post-liming operation. Compacting of a waste containing water consists, via addition of CaO, in coating said waste in a dry matrix of $Ca(OH)_2$. Compacting of a waste that does not contain water comprises mixing said waste with CaO then adding $H_2O$ in order to obtain the same dry matrix. Compacting, in particular carried out in a mold having nonstick walls, results in the formation of shaped products.

SUMMARY OF THE INVENTION

There is a need as regards the technical problem of concentrating, separating and drying, using quicklime or hydrated lime, solid products contained in solid matter/liquid mixtures or in suspensions of which the liquid (water or an organic solvent) is capable of reacting with the quicklime. The ideal thing would be to have, on the one hand, the advantages of the operations known as pre-liming and post-liming, without their aforementioned drawbacks and, on the other hand, to use a homogeneous lime/solid matter to be recovered mixture (i) in said solid matter/liquid mixture or suspension to be treated then (ii) in the separation residue without restrictive additional handling and without violent reaction of CaO with water or said organic liquid of said mixture or of said suspension, said violent reaction having the disadvantage of being capable of generating dust and of producing lime agglomerates that prevent the desired homogeneity from being obtained.

Also, it is proposed to supply a novel technical solution to the problem of treating solid matter/liquid mixtures or suspensions comprising a liquid capable of reacting with CaO, with the aim of concentrating, decontaminating (i.e. "sanitizing" or cleaning up), drying and recovering the dry solids contained in said mixtures or suspensions, especially aqueous suspensions, on the one hand.

It is also proposed to apply this novel technical solution more particularly to the treatment of sludges, on the other hand.

In addition, it is proposed to provide a method for treating said sludges in order to concentrate, decontaminate, dry and recover them, for example with the aim of spreading them without any risk of polluting the environment, especially for improving or enriching cultivable soils.

Finally, it is proposed to provide, as novel industrial products (a) purified sludges obtained according to this method, and (b) a combination of a DRQL with at least one iron and/or aluminum salt.

This objective has been achieved thanks to the use of a particular reactive lime, namely a delayed reactivity partly prehydrated quicklime (DRQL), capable of being obtained according to the teaching of the aforementioned document FR 2 841 895 A, and which is involved in the pre-liming operation through the protective $Ca(OH)_2$ that it contains, then in the post-liming operation through the CaO that it contains.

In what follows, the term "suspension" encompasses, for convenience, any actual suspension (i.e. presence of solid particles dispersed in the liquid) and any solid matter/liquid mixture in which at least one portion of the liquid matter (however tiny it is) is capable of being dispersed (especially by stirring) in the liquid. This is because, even if the solid particles are substantially gathered together in said solid matter/liquid mixture, it is sufficient to stir it in order to obtain the dispersion of the solid particles that it contains; as a variation, it is possible to draw off a portion of the supernatant (or in certain cases of the subnatant) and put the remaining solids/liquid composition under stirring in order to have said dispersion. If necessary, said supernatant (or subnatant) drawn off in this way, which may be cloudy, may itself be reprocessed and concentrated.

According to a first aspect of the invention, a novel use of quicklime is recommended in the concentration, separation and desiccation of solid matter capable of being dispersed (especially with stirring, the dispersion possibly being at least partial) in a liquid, said use being characterized in that a delayed reactivity partly prehydrated quicklime (DRQL) is required, which is composed of two essential components, CaO and $Ca(OH)_2$, arranged in such a way that, in the presence of water, the reaction (1) between the quicklime CaO and the water:

$$CaO + H_2O \rightarrow Ca(OH)_2 \quad (1)$$

is temporarily delayed by the hydrated lime $Ca(OH)_2$, the hydrated lime of the DRQL being used for the flocculation or concentration of the solid matter before separation, and the quicklime of said DRQL being used for the desiccation of said solid matter during or (better still) after separation.

According to a second aspect of the invention, a novel method is recommended for the concentration, separation, desiccation and decontamination of the solids of a sludge using lime with the aim of separating its solids, said method being characterized in that it comprises the steps consisting in:

(α) contacting, with stirring, the delayed reactivity partly prehydrated quicklime (DRQL) with the sludge to be treated, for 0.4 to 30 minutes, preferably for a duration of less than or equal to 10 minutes, and better still for a duration of 2 to 3 minutes, in an amount of at least one part by dry weight of said DRQL per 100 parts by dry weight of solids contained in said sludge, the $Ca(OH)_2$ of the particles of said DRQL being used for the concentration or flocculation of said solids;

(β) separating, especially by filtration, centrifugation or settling, the resulting suspension in order to obtain a solid material being in the form of a first wet cake, which is a homogeneous mixture of said concentrated solids, of said DRQL and of water; then, (γ) making or letting the CaO of said DRQL, which is contained in said solid material thus separated, react with the water of said solid material.

According to another aspect of the invention, a solid material derived from a sludge is recommended as a novel industrial product, which is capable of being obtained according to this method, said material being characterized in that it has been purified using a DRQL composed of 40 to 98% by weight of CaO and of 60 to 2% by weight of $Ca(OH)_2$, preferably composed of 80 to 92% by weight of CaO and of 20 to 8% by weight of $Ca(OH)_2$, and better still composed of 85 to 90% by weight of CaO and of 15 to 10% by weight of $Ca(OH)_2$, having an average particle size such that $20\ \mu m \leq d_{50} \leq 200\ \mu m$ and being used (i) in the form of a powder or (ii) in the form of an aqueous suspension having a concentration greater than or equal to 10% by weight.

Finally, according to another aspect of the invention, for treating a sludge, a combination of (a) a DRQL, composed of 40 to 98% by weight of CaO and of 60 to 2% by weight of $Ca(OH)_2$, preferably composed of 80 to 92% by weight of CaO and of 20 to 8% by weight of $Ca(OH)_2$, and better still composed of 85 to 90% by weight of CaO and of 15 to 10% by weight of $Ca(OH)_2$, having an average particle size such that $20\ \mu m \leq d_{50} \leq 700\ \mu m$ and being used (i) in the form of a powder or (ii) in the form of an aqueous suspension having a concentration greater than or equal to 10% by weight;

with (b) at least one metal salt, especially an $Fe^{3+}$ salt and/or an $Al^{3+}$ salt, preferably $FeCl_3$, $Al_2(SO_4)_3$ and/or basic aluminum chloride, is recommended in which the DRQL and the metal salt are packaged separately, in the form of two different products, or together, in the form of a single product resulting from their mixing, said combination being especially useful for (i) separating solid/water matter from an industrial sludge, from an urban sludge, from a wastewater sludge, from a biological sludge, from an agricultural sludge, such as liquid manure, or from a dredging sludge, and (ii) decontaminating, drying and grinding of the formulation of solid matter resulting from said separation.

BRIEF DESCRIPTION OF THE DRAWINGS

In the appended drawing, the sole FIGURE (FIG. 1) allows the reactivities of several limes to be compared for the sludge temperature (in ° C.) on the Y-axis as a function of the reaction duration (in seconds) on the X-axis.

DETAILED DESCRIPTION OF THE INVENTION

Figure 1:
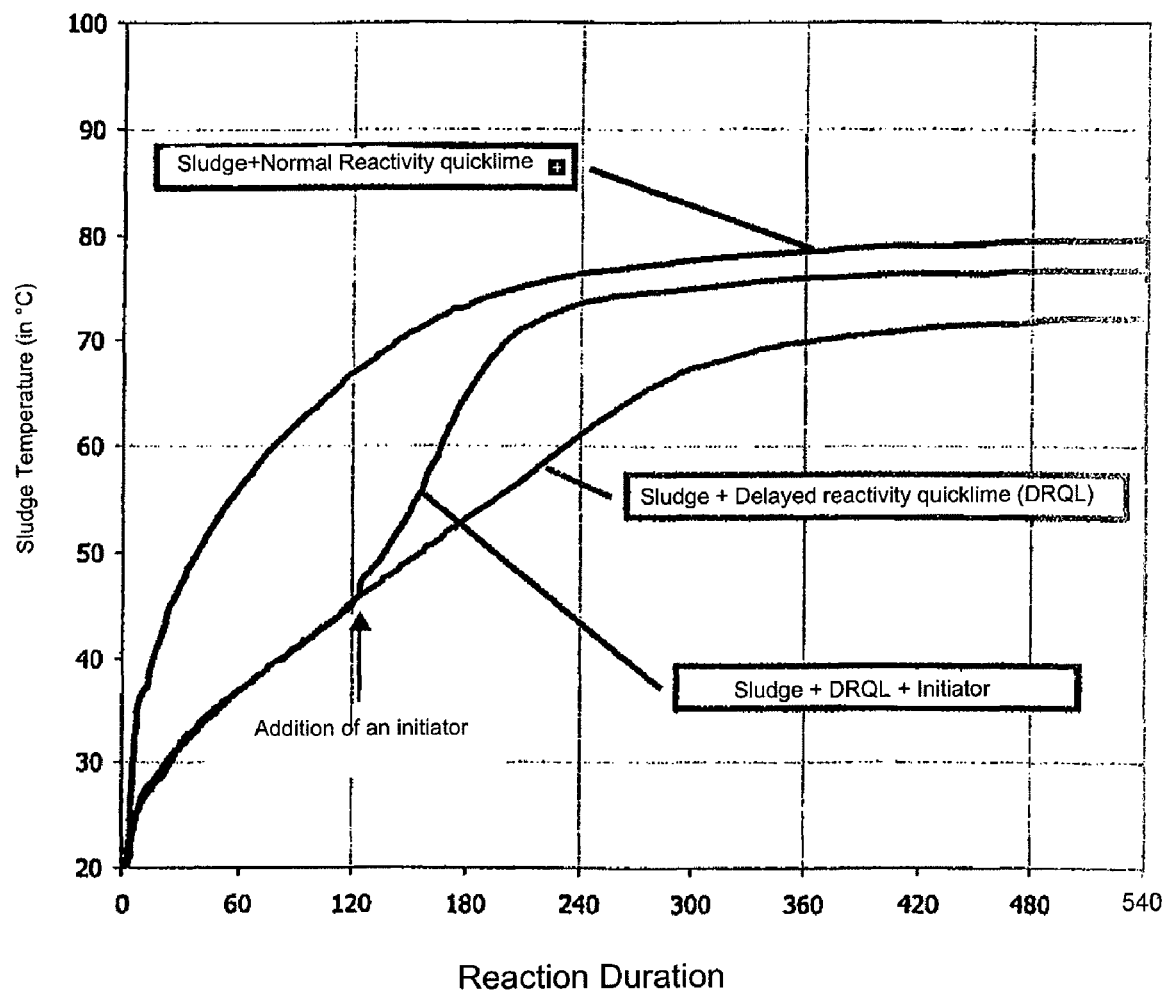

In the expression "delayed reactivity quicklime", it is understood that the CaO contained in the DRQL has, in contact with water, a delayed reactivity of around a few minutes to two hours or even longer according to FR 2 841 895 A, relative to that of non-prehydrated quicklime. The delay in the reactivity increases with the $Ca(OH)_2$ content of the DRQL. Moreover, it is a function of the concentration and the type of the constituent matter of the suspension that it is desired to treat.

The liquid of the suspension, which is suitable according to the invention, is composed of or contains water, on the one hand, or is composed of one or more solvents that may react with the CaO of the DRQL, on the other hand. For convenience, the suspensions in question hereinafter, especially in the examples, are aqueous suspensions.

As regards the particle size:

$$d_x \leq y\ (\text{in}\ \mu m)$$

is understood here to mean the fact that x % by weight of the particles concerned have a size less than or equal to y μm.

The dry content (DC) corresponds to the percentage of dry matter in a suspension. It is calculated here from the equation:

$$DC = 100\ \frac{MSO}{MSU}$$

where MSO is the mass of solid matter contained in the suspension, and MSU is the total mass of the suspension.

The increase in the dryness is also expressed as a percentage and corresponds to the difference between the DC of the suspension before separation and the DC of the suspension after separation:

increase in dryness=$DC_{before}-DC_{after}$

According to the invention, a DRQL, e especially as described in the aforementioned prior document FR 2 841 895 A, is added upstream of the step for separating the solids from the liquid.

When the DRQL is added to the suspension during the pre-liming step, each quicklime core does not react with the water contained in the suspension, with regard to the lag phase of the reaction (1), due to its protective $Ca(OH)_2$ layer. This circumstance makes it possible to easily obtain a homogeneous mixture between the lime and the suspension, and to avoid disturbing the solids/liquid separation method. Moreover, surprisingly, the contact between the $Ca(OH)_2$ layer and the suspension creates a sufficiently high pH to promote the solids/liquid separation, if necessary in combination with metal salts. The particle size of this lime also makes it possible to increase the porosity of the cakes and favors the performances of mechanical separation systems, such as centrifuges, filter presses and belt filters.

After separation, the $Ca(OH)_2$ layer is resorbed and releases the quicklime core that it covers. This CaO core will then react with the residual water present in the separation cake or residue. This reaction will produce heat, generate a high pH and thus ensure sanitization. Moreover, this reaction will further increase the dry content of the separation cake or residue. The treatment is then better still performing and more economical than that described in the technical solutions known from the prior art, because at the time of the reaction, the lime is already well dispersed homogeneously in said separation cake or residue, and a long and costly mixing step is avoided. In brief, the invention finally has the advantage of only using a single particular lime, the DRQL, to implement, in a combined and successive manner, the pre-liming then post-liming operations.

As indicated above, the DRQL is composed of 40 to 98% by weight of CaO and of 60 to 2% by weight of $Ca(OH)_2$. Preferably the DRQL will be composed of 80 to 92% by weight of CaO and of 20 to 8% by weight of $Ca(OH)_2$, and better still of 85 to 90% by weight of CaO and of 15 to 10% by weight of $Ca(OH)_2$.

Said DRQL is, according to the invention, used (i) in powder form or (ii) in the form of an aqueous suspension having a concentration greater than or equal to 10% by weight. When it is involved in the form of an aqueous suspension, said DRQL will advantageously be at a concentration which may be greater than or equal to 50% by weight, and better still at a concentration of 60 to 90% by weight. In brief, used in the form of an aqueous suspension, said DRQL will be at a concentration of 5 to 90% by weight, the high concentrations (for example around 75 to 90% by weight) possibly being obtained by adding a superplasticizer known in the art.

The technical solution of the invention applies most particularly to the treatment of sludges, especially to:
 industrial sludges;
 dredging sludges;
 agricultural sludges, such as liquid manures;
 biological sludges (possibly containing microorganisms capable of being pathogenic for the environment);
 sludges derived from the treatment of wastewaters; and
 urban sludges.

The DRQL is first mixed with the suspension to be concentrated and to be treated, optionally already added to which is the solution of metal salts, ideally of ferric chloride, aluminum sulfate and/or basic aluminum chloride [remembering that basic aluminum chloride, also known as "aluminum oxychloride", is a product having the formula: $Al_2(OH)_3 CL \cdot 2H_2O$ according to the *Merck Index*, 13*th edition*, 2001]. The mixing may be carried out by any technique, but preferably in a kneader. During the mixing phase, the particle size of the DRQL does not change at all or very little. It will therefore be adjusted to optimize the operation of the equipment and the performance of the desiccation method. As regards the particle size of the DRQL, it is a question of finding an optimized compromise between the need to have particles of small size to ensure a good distribution of the lime and the need to have particles of sufficient size in order to increase the porosity of the cake or residue and to promote the solids/liquid separation.

The technical solution recommended here is that said DRQL used has a particle size of less than 5 mm. A DRQL is recommended, in order to have a good porosity in the separation cake or residue, preferably having an average particle size between 20 µm and 1 mm. In practice, the particles having a size greater than 1 mm will be removed in order to avoid settling phenomena especially for suspensions having low viscosities. Except for special cases, the $d_{50}$ will not be chosen to be less than 20 µm in order to prevent decreasing the porosity of the separation cakes or residues.

The average particle size of the DRQL, which is most particularly recommended according to the invention, is such that $20 \mu m \leq d_{50} \leq 700 \mu m$. If it is desirable, it is even possible to sieve the DRQL in order to remove the particles having a size greater than or equal to 700 µm, then those having a size of less than or equal to 20 µm.

The lime will be proportioned depending on the dry content of the emulsion to be treated, the expected rheological characteristics for the final concentrated product, and the pH or temperature constraints imposed especially by the sanitization of said final product. In practice, at least one part by weight of DRQL per 100 parts by dry weight of the solids contained in the emulsion to be treated will be used.

The lime according to the invention will advantageously be used, especially for treating an industrial, urban or biological sludge, according to a quantity of DRQL, expressed in CaO equivalents, of 3 to 100 parts by weight per 100 parts by dry weight of solids, and better still of 20 to 100 parts by weight per 100 parts by dry weight of solids, contained in the sludge to be treated, said DRQL occurring
 (i) in the form of a powder; or
 (ii) in the form of an aqueous suspension having a concentration greater than or equal to 10% by weight, preferably having a concentration greater than or equal to 50% by weight, and better still (in combination with a superplasticizer) having a concentration of 75 to 90% by weight.

In step (α) of the method of the invention, the DRQL is contacted with the sludge to be treated with stirring, for 0.4 to 30 minutes, in particular for a duration less than or equal to 10 minutes, and especially for 2 to 3 minutes, the $Ca(OH)_2$ of the particles of said DRQL being used for the concentration or flocculation of said solids.

A duration of less than or equal to 10 minutes is especially recommended in order to ensure the integrity of the quicklime cores of the DRQL during step (α). Thanks to its particle size, said DRQL acts as a mineral on the porosity of the separation cake or residue and favors increases in the dryness.

In step (β) of this method, the wet material obtained, which includes the solids from the initial suspension, the DRQL particles and water, are separated by filtration, centrifugation or settling. This operation can be carried out using a suitable device, for example a centrifuge, a filter press or a belt filter, or even a settling tank.

In step (γ) of the method of the invention, it is possible to let the CaO of the DRQL react with the water of the separation cake or residue. However, in order to promote the solids/liquid separation and/or to avoid too lengthy waiting times, the possibility is suggested according to the invention of producing the reaction between CaO and water in the concentrated suspension. There is also an interest in being able to localize the reaction in a place where it is possible to control and develop the release of heat and optionally of gas, such as in the case of the $NH_3$ released during the treatment of suspensions containing ammonium salts, such as liquid manures.

Thus the reaction from step (γ) may advantageously be initiated:
- by thermal means, especially via a supply of dry steam;
- by sonic means, especially via an ultrasound field; or
- by chemical means, especially with a substance chosen from the group formed by mineral acids, organic acids, alkali metal salts, alkaline-earth metal salts, polyols and mixtures thereof.

The initiation may be carried out by thermal or sonic activation or by adding a chemical initiator. The objective of this initiation is to destroy the calcium hydroxide layer and to release the quicklime cores. The chemical initiators are substances that react with the calcium hydroxide or that may change its solubility. They will preferentially be chosen from the group comprising inorganic acids (especially HCl or $HNO_3$), organic acids, alkali metal salts (especially NaCl), alkaline-earth metal salts (especially $CaCl_2$), polyols (especially sorbitol, glycerol, pentaerythrol and polyalkylene glycols) and mixtures thereof. They will be added in solid or liquid form or else in the form of a suspension. Practically, the chemical initiator may be added as a solution (especially 1 wt %) in the water for washing the wet separation cake. The type and the amount of the chemical initiator will be adjusted according to the desired effect.

The initiation of the reaction from step (γ) may be initiated, where appropriate, during the separation from step (β) or better still, after said step (β).

During the implementation of step (γ), the dryness increases gradually to reach a plateau. Hydration of the quicklime releases heat (1160 kJ per kg of CaO at 20° C.). The temperature rises associated with this release are larger when the heat losses are minimized. It is possible, for example, to control the method of the invention so as to initiate the reaction from step (γ) when the suspension that is treated is stored in a thermally insulated place. The temperatures required for thermal sanitization (i.e. a temperature greater than 55° C. for 75 minutes) will be achievable without additional treatment.

As a variation, depending on the nature of the solids from the suspension to be treated, it is possible to omit the separation step (β). In this case a homogeneous suspension or a solid product that is wet is obtained (see Ex. 8 and Ex. 9 hereinbelow). The removal of said step (β) is perfectly suited to the treatment of suspensions of stercoraceous matter.

ADVANTAGE OF THE INVENTION

The treatment of a sludge according to a method of the invention using lime, by replacing
(a) the limewater; or
(b) the powdered quicklime,
used in the conventional methods of pre-liming or post-liming, with powdered DRQL offers numerous advantages, namely in particular:

formation of a homogeneous mixture during the intervention of the $Ca(OH)_2$ of the DRQL then that of the CaO of said DRQL;

absence of the risk of a violent reaction, whereas the quicklime used previously gives a violent reaction;

a reduction in the time and energy for obtaining a perfectly homogeneous final product;

the absence of a special preparation unit, whereas such a unit is necessary in the case of limewater; and accuracy of proportioning, which is greater than that of the pre-liming technique using limewater.

EXAMPLES

The comparison of the results from examples 1-5 according to the invention with the corresponding comparative examples A1-A5, demonstrates that the material derived from a sludge has an increase in dryness greater than or equal to 2% relative to the previous pre-liming or post-liming techniques.

Further advantages and features of the invention will be better still understood on reading the embodiment examples (Ex. 1-Ex. 9) and comparative examples (A1-A5 corresponding respectively to examples 1 to 5) that follow. Of course, all of these facts are not limiting but are provided by way of illustration.

Example 1

A biological sludge of industrial origin, having a solids concentration of 2.2% by dry weight, was mixed with stirring in the 1 $m^3$ tank of a centrifuge (operating at 20 $m^3$/h) with a DRQL having a CaO/$Ca(OH)_2$ weight ratio of 90/10 and a particle size such that 20 µm$\leq d_{50} \leq$200 µm, in an amount of one part by dry weight of DRQL per one part by dry weight of solids, here being 22 kg of DRQL per 1 $m^3$ of sludge to be treated. An aqueous solution containing 500 g/l of ferric chloride was added simultaneously to the tank in an amount of 0.8 L of this solution per 1 $m^3$ of sludge to be treated. After centrifuging, a first wet cake was obtained having a DC of 37%, in which the DRQL was distributed uniformly. This first wet cake was left to stand so that the reaction of the CaO from the DRQL with the water of said first cake was carried out. After 72 h, it was observed that the dryness of the final cake had increased; it was 42% and remained constant beyond 72 h.

Comparative Example A1

The biological sludge from example 1 was treated conventionally, in the tank of the same centrifuge, with an organic polymer flocculant (here an acrylic acid/acrylamide copolymer), at an amount of 15 g by dry weight of flocculant per 1 kg of solids by dry weight of said sludge. A first wet separation cake was obtained, that was recovered and had a DC of 18%. This first cake was then mixed with the quicklime in an amount of one part by dry weight of CaO per one part by dry weight of solids of said initial sludge. After mixing, the final cake that was obtained was disintegrated by reaction of the quicklime and had a DC of 34% which, measured after 72 h, remained constant.

Example 2

The method of example 1 above was followed, but with the difference that (a) 0.55 parts by dry weight of DRQL (i.e. 0.5 parts by weight of CaO) per one part by dry weight of solids of the initial sludge, and (b) 0.4 L (instead of 0.8 L) of aqueous FeCl$_3$ solution per 1 m$^3$ of sludge to be treated were used. The second cake that was recovered had a DC of 31%. After 72 h, it was observed that the DC had increased and was 34% and remained constant beyond 72 h.

Comparative Example A2

The method of the comparative example A1 was followed but with the difference that, for treating the first cake, which had a DC of 18%, a quantity of 0.5 (instead of 1) parts by weight of quicklime per one part by dry weight of solids from the sludge was used. A final cake having a DC of 27.5% was obtained, which measured after 72 h, remained constant.

Example 3

The biological sludge from example 1 was treated in a filter press with addition of 1 kg of DRQL [having a CaO/Ca(OH)$_2$ weight ratio of 85/15 and a particle size such that 20 μm≦d$_{50}$≦200 μm] in an amount of one part by dry weight of DRQL per one part by dry weight of solids, here being 22 kg of DRQL per 1 m$^3$ of sludge to be treated. An aqueous solution having 500 g/l of FeCl$_3$ was added simultaneously in an amount of 0.8 l per 1 m$^3$ of sludge to be treated. The DC of the final cake obtained was 42%. After 72 h, it was observed that the DC had increased and was 48%.

Comparative Example A3

The biological sludge from example 1 was treated conventionally in a filter press by adding thereto 1 kg of Ca(OH)$_2$ per 1 kg of dry matter contained in this sludge. The first filtration cake had a DC of 41% and a structure that did not allow the post-liming operation.

Example 4

A biological sludge of urban origin having a dry matter content of 2.4% by weight was mixed, with stirring, in a 1 m$^3$ tank with the DRQL of example 1 added in an amount of 0.5 parts by weight per one part by weight of dry matter, being 12 kg per 1 m$^3$ of sludge to be treated. An aqueous solution having 500 g/l of FeCl$_3$ was added simultaneously in an amount of 0.5 l per 1 m$^3$ of sludge to be treated. The DC of the final cake obtained by separating on a belt filter (operating with a flow rate of 6 m$^3$/h) was 34%. After 72 h, it was observed that the DC had increased and was 37%.

Comparative Example A4

The sludge from example 4 was treated conventionally using the same belt filter and adding thereto 5 g of polymer (polyacrylamide) per 1 kg of dry matter. The first filtration cake, thus obtained, was mixed with quicklime in an amount of 0.5 kg of CaO per 1 kg of dry matter from the initial sludge. After mixing, the cake disintegrated by the operation had a DC of 32% which remained constant after 72 h.

Example 5

400 liters of biological sludge of urban origin having a dry matter content of 3.5% by weight were mixed, with slow stirring, in a 500 liter tank with a solution of FeCl$_3$ in an amount of eight parts of FeCl$_3$ per 100 parts of dry matter. The DRQL from example 1 was then introduced directly, as a powder, with slow stirring in an amount of 45 parts of DRQL per 100 parts of dry matter. The perfectly homogeneous mixture was pumped without any time delay through a filter press. The filtrate was immediately clear, the filtration time was 65 minutes and the dryness of the cake was 35%.

Comparative Example A5

The sludge from example 5 was treated conventionally via ferric chloride and lime introduced in the form of hydrated lime water (the use of a powdered quicklime would not allow a homogeneous mixture that is compatible with the filtration on a filter press to be obtained). The mixture was pumped through the filter press after a delay of 30 to 40 minutes in order to obtain an immediate clarification. The filtration time was 100 minutes and the final dryness was 33%.

Example 6

A homogeneous liquid pig manure having a dry matter concentration of 5.5% by weight was mixed, with stirring, in a 1 m$^3$ tank of a centrifuge, operating at a flow rate of 4 m$^3$/h, with the DRQL from example 3 added in an amount of 10 kg of DRQL per 1 m$^3$ of sludge to be treated. The centrifuged liquid manure immediately appeared in the form of a slightly wet divided powder. After 24 hours, this powder was perfectly dry and easy to handle; its DC was 39%.

Example 7

Initiation of the Post-Liming Reaction by Chemical Means

Measurement of the reactivities of the limes was carried out according to the standardized method EN459-2. The main modification used here relates to the replacement of demineralized water with a biological sludge having a dry solids content of 2.7%. 150 g of lime (CaO quicklime or DRQL according to example 1) were roughly immersed in 600 g of this sludge at 20° C. After the introduction, the temperature of the mixture resulting from stirring was measured continuously. The temperature increase curves are given in FIG. 1. The initiation additive (HCl) was added, at time A, in an amount of 1% by weight relative to the mass of CaO used.

In the sludge temperature (in ° C.) as a function of the reaction time (in seconds) system of FIG. 1, curve 1 relates to the sludge to which normal quicklime has been added, curve 3 relates to the sludge to which DRQL has been added and curve 2 shows the effect of the initiation additive after its incorporation at time A into the sludge+DRQL mixture.

Example 8

The raw material was an aqueous suspension of stercoraceous matter. It mainly derived from industrial rabbit abattoirs and had first been centrifuged to remove the solid portions.

This aqueous suspension was mixed continuously and with stirring with the DRQL from example 3 in an amount of 5 to 8 parts by weight of DRQL per 100 parts by weight of stercoraceous matter that it contained. The DRQL was introduced directly into the mixer in powder form. The delay of the reaction (1) made it possible to obtain a homogeneous mixture having constant viscosity and the deodorization effect was immediate.

The homogeneous mixture thus obtained was transferred into a storage unit where the reaction (1) started and enabled said mixture to be brought to a temperature between 40 and 70° C. depending on the amount of DRQL added. The increase in the viscosity after the reaction (1) also depended on the amount of DRQL added: with up to eight parts of DRQL per 100 parts of stercoraceous matter, the resulting mixture remained liquid and was treated as such in the chosen disposal system.

Example 9

The method from example 8 was reproduced, with the difference that 15 parts (instead of 5 to 8 parts) of DRQL were added per 100 parts of stercoraceous matter. The increase in the amount of DRQL used had the result of making, via the initiation of reaction (1) during storage, the temperature of the resulting mixture climb to more than 95° C. and of obtaining a solid structure enabling the mixture to be stored on the ground with an angle of repose of 45°. This type of treatment may advantageously be used depending on the chosen disposal system.

What is claimed is:

1. A method for the separation, concentration and desiccation of solid matter capable of being dispersed in a liquid, by providing a delayed reactivity partly prehydrated quicklime (DRQL), which is composed of two essential components, CaO and $Ca(OH)_2$ and is associated with at least one metal salt, wherein said metal salt is a $Fe^{3+}$salt or an $Al^{3+}$salt, the DRQL is arranged in such a way that, in the presence of water, a reaction (1) between the water and the quicklime (CaO):

$$CaO + H_2O \rightarrow Ca(OH)_2 \quad (1)$$

is temporarily delayed by hydrated lime $Ca(OH)_2$, wherein the hydrated lime of the DRQL flocculates or concentrates the solid matter before separation, and the quicklime of said DRQL desiccates said solid matter during or after said separation.

2. The method as claimed in claim 1, wherein said DRQL comprises 40 to 98% by weight of CaO and of 60 to 2% by weight of $Ca(OH)_2$.

3. The method as claimed in claim 1, wherein said DRQL has a particle size of less than 5 mm.

4. The method as claimed in claim 1, wherein said DRQL comprises 80 to 92% by weight of CaO and 20 to 8% by weight of $Ca(OH)_2$.

5. The method as claimed in claim 1, wherein said DRQL comprises 85 to 90% by weight of CaO and 15 to 10% by weight of $Ca(OH)_2$.

6. The method as claimed in claim 1, wherein said DRQL has an average particle size between 20 μm and 1 mm.

7. The method as claimed in claim 1, wherein said DRQL has an average particle size such that 20 μm≦$d_{50}$≦700 μm.

8. A method for the separation, concentration and desiccation of solid matter capable of being dispersed in a liquid, by providing a delayed reactivity partly prehydrated quicklime (DRQL), which is composed of two essential components, CaO and $Ca(OH)_2$ and is associated with at least one metal salt, wherein said metal salt is at least one selected from the group consisting of $FeC_3$, $Al_2SO_4)_3$ and an $Al^{3+}$salt, the DRQL is arranged in such a way that, in the presence of water, a reaction (1) between the water and the quicklime (CaO):

$$CaO + H_2O \rightarrow Ca(OH)_2 \quad (1)$$

is temporarily delayed by hydrated lime $Ca(OH)_2$, wherein the hydrated lime of the DRQL flocculates or concentrates the solid matter before separation, and the quicklime of said DRQL desiccates said solid matter during or after said separation.

* * * * *